(12) United States Patent
Ohwada et al.

(10) Patent No.: US 10,988,595 B2
(45) Date of Patent: Apr. 27, 2021

(54) URETHANE DECOMPOSING METHOD AND URETHANE DECOMPOSING AGENT

(71) Applicants: Obihiro University of Agriculture and Veterinary Medicine, Obihiro (JP); Nihon Plast Co., Ltd., Fujinomiya (JP)

(72) Inventors: Takuji Ohwada, Obihiro (JP); Kazuyuki Endo, Fujinomiya (JP)

(73) Assignees: OBIHIRO UNIVERSITY OF AGRICULTURE AND VETERINARY MEDICINE, Obihiro (JP); NIHON PLAST CO., LTD., Fujinomiya (JP)

( * ) Notice: Subject to any disclaimer, the term of this patent is extended or adjusted under 35 U.S.C. 154(b) by 204 days.

(21) Appl. No.: 15/036,980

(22) PCT Filed: Dec. 4, 2014

(86) PCT No.: PCT/JP2014/082135
§ 371 (c)(1),
(2) Date: May 16, 2016

(87) PCT Pub. No.: WO2015/083797
PCT Pub. Date: Jun. 11, 2015

(65) Prior Publication Data
US 2016/0257800 A1 Sep. 8, 2016

(30) Foreign Application Priority Data

Dec. 4, 2013 (JP) .............................. JP2013-250967
May 27, 2014 (JP) .............................. JP2014-108764

(51) Int. Cl.
| | | |
|---|---|---|
| C08J 11/10 | (2006.01) | |
| C12N 1/20 | (2006.01) | |
| C12N 1/00 | (2006.01) | |
| C08J 11/26 | (2006.01) | |
| C08J 11/18 | (2006.01) | |
| C08J 11/24 | (2006.01) | |
| C08J 11/06 | (2006.01) | |
| C12R 1/465 | (2006.01) | |
| A62D 3/02 | (2007.01) | |
| A62D 101/26 | (2007.01) | |

(52) U.S. Cl.
CPC .............. *C08J 11/105* (2013.01); *A62D 3/02* (2013.01); *C08J 11/24* (2013.01); *C08J 11/26* (2013.01); *C12N 1/20* (2013.01); *C12R 1/465* (2013.01); *A62D 2101/26* (2013.01); *C08J 2375/04* (2013.01); *Y02W 30/62* (2015.05)

(58) Field of Classification Search
CPC . C08J 11/105; C08J 11/24; C08J 11/26; C08J 2375/04; C12R 1/465; A62D 3/02; A62D 2101/26; C12N 1/20; Y02W 30/62
See application file for complete search history.

(56) References Cited

U.S. PATENT DOCUMENTS

| | | | | |
|---|---|---|---|---|
| 6,313,194 | B1 * | 11/2001 | Yagi ....................... | C12N 11/04 523/124 |
| 2005/0020701 | A1 * | 1/2005 | Saya ...................... | C08G 18/83 521/49 |
| 2011/0014664 | A1 * | 1/2011 | Tiwari ................. | C07D 305/12 435/123 |

FOREIGN PATENT DOCUMENTS

| | | |
|---|---|---|
| JP | 2004-339438 A | 12/2004 |
| JP | 2005-048098 A | 2/2005 |
| JP | 2005-068313 A | 3/2005 |
| JP | 2006-158237 A | 6/2006 |
| JP | 2010-220610 A | 10/2010 |
| JP | 2010220610 | * 10/2010 |

OTHER PUBLICATIONS

English translation of International Search Report for PCT/JP2014/082135 (2 pgs.).
English translation of the International Preliminary Report on Patentability and Written Opinion of the International Searching Authority for PCT/JP2014/082135 (11 pgs.).

* cited by examiner

*Primary Examiner* — Blaine Lankford
*Assistant Examiner* — Lauren K Van Buren
(74) *Attorney, Agent, or Firm* — Flynn Thiel, P.C.

(57) ABSTRACT

The purpose of the present invention is to provide a novel urethane decomposing method by which urethane in the environment is treated efficiently and at a low cost, and a urethane decomposing agent. The above purpose is attained by employing a urethane decomposing method including: a step of treating a urethane-containing material to be treated using an unsaturated fatty acid; and a step of making a microorganism belonging to a *Streptomyces* genus and exhibiting urethane decomposing function, to act on the material treated using the unsaturated fatty acid.

20 Claims, No Drawings

URETHANE DECOMPOSING METHOD AND URETHANE DECOMPOSING AGENT

FIELD OF THE INVENTION

The present invention relates to a method for decomposing urethane using a microorganism and a urethane decomposing agent.

DESCRIPTION OF THE RELATED ART

Polyurethane is a polymer having a urethane bond and is also called a urethane resin. The polyurethane is gradually decomposed under the influence of hydrolysis by moisture, nitrogen oxide (NOx) in the air, salinity, ultraviolet, heat, microorganisms, and the like, and generates a compound that is harmful to the human body and the aquatic organisms. Since there is a possibility that leaked polyurethane can cause serious environmental pollution, urethane is generally recovered after prevention treatments of, for example, causing the urethane to be adsorbed in soil and sand, or covering the urethane, is encapsulated in a container and is then subjected to treatment. Although a recycle system of polyurethane has been developed, about 40% of waste polyurethane is still landfilled. Hereinafter, the "polyurethane" is sometimes simply referred to as "urethane".

The inventors of the present invention found a novel microorganism exhibiting an adsorbing function and a decomposing function to urethane in the ground and filed a patent application (Japanese Patent Publication No. 2010-220610). The microorganism was determined as a novel actinomycete belonging to a *Streptomyces* genus based on microbial properties and DNA analysis. This microorganism has adsorbability to urethane. Thus, urethane particles dispersed in water can be bound to one another and aggregated and can be effectively removed (adsorbed, purified).

SUMMARY OF THE INVENTION

1. Problems to be Solved by the Invention

The microorganism described in Japanese Patent Publication No. 2010-220610 exhibits an adsorption capacity and a decomposing function to urethane. However, in order to industrially use the microorganism, the urethane decomposition rate is required to be further improved, and there is a room for improvement of this point.

Hence, the present invention is intended to provide a novel urethane decomposing method by which urethane in the environment is treated efficiently and at a low cost, and a urethane decomposing agent.

2. Means for Solving the Problems

In order to solve the aforementioned problem, the inventors of the present application conducted earnest studies of changing urethane to be in the state of being easily decomposed by the microorganism. Then, they focused on the point where it is said that the steering mechanism of an automobile, which steering mechanism contains urethane as a main component, is degraded by human sebum in addition to ultraviolet, cosmetics, and the like. As a result, they found that one of main components of human sebum is oleic acid, and pretreating urethane using such an unsaturated fatty acid is effective. Thus, they completed the present invention.

That is, the following configuration is employed in the present invention.

(1) A urethane decomposing method including: a step of treating a urethane-containing material to be treated using an unsaturated fatty acid; and a step of allowing a microorganism, belonging to a *Streptomyces* genus and exhibiting urethane decomposing function, to act on the material treated using the unsaturated fatty acid.

(2) The urethane decomposing method according to (1) above, wherein in the step of treating the material to be treated using the unsaturated fatty acid, the unsaturated fatty acid and alcohol are mixed for use.

(3) The urethane decomposing method according to (1) or (2) above, including the step of treating the material to be treated using alcohol before the step of treating the material to be treated using the unsaturated fatty acid.

(4) The urethane decomposing method according to any one of (1) to (3) above, wherein the microorganism belonging to a *Streptomyces* genus is a microorganism specified by Accession No. FERM BP-21770 as discussed below.

(5) The urethane decomposing method according to any one of (1) to (4) above, wherein the unsaturated fatty acid is a mixture of one or more kinds selected from the group consisting of oleic acid, linoleic acid, and erucic acid.

(6) The urethane decomposing method according to any one of (1) to (5) above, wherein the alcohol is a mixture of one or more kinds selected from the group consisting of methanol, ethanol, 1-propanol, 2-propanol, 1-butanol, 2-butanol, 2-methyl-1-butanol, and 2-methyl-2-butanol.

(7) The urethane decomposing method according to any one of (1) to (6) above, wherein the microorganism is made to act on the material to be treated while treating the material to be treated using the unsaturated fatty acid.

(8) A urethane decomposing agent containing the microorganism and the unsaturated fatty acid, according to any one of (1) to (7) above.

(9) The urethane decomposing agent according to (8) above, further containing alcohol.

The present invention can provide a novel urethane decomposing method by which urethane in the environment is treated efficiently and at a low cost, and a urethane decomposing agent.

DETAILED DESCRIPTION OF THE PREFERRED EMBODIMENTS

Urethane Decomposing Method

The urethane decomposing method according to the present invention includes: a step of treating a urethane-containing material to be treated using unsaturated fatty acid; and a step of making a microorganism belonging to a *Streptomyces* genus and exhibiting urethane decomposing function to act on the material treated using the unsaturated fatty acid. According to this method, urethane leaked in the environment and raw materials of urethane contained in industrial wastewater that contains organic solvents can be treated efficiently and at a low cost. Recovered urethane can be recycled, resulting in effective use of resources.

Each step is described in detail below.

Step of Treating Urethane-Containing Material to be Treated Using an Unsaturated Fatty Acid The urethane means a compound obtained by dehydration condensation of an amino group and an alcohol group via carbonyl, i.e., carbamic ester. Urethane to be decomposed in the present invention includes all of urethanes having a urethane bond in a molecular structure, including a low-molecular-weight urethane such as ethyl carbamate and a polymer such as polyurethane.

The polyurethane is a polymer obtained by polymerization using a urethane bond and is used in a coating, adhesive, urethane foam, textile goods, shoes, automobile parts, construction materials, and the like. The polyurethane includes straight-chain polyurethane, branched polyurethane, polyurethane including cross-linking, elastic polyurethane, polyurethane foam, and the like and can be broadly divided into esters and ethers. In the present invention, the polyurethane to be decomposed is not limited to particular polyurethanes, but it is desirable to use urethane having a relatively large particle size to the extent that a state where the urethane, which is emulsified because of the large particle size, becomes transparent due to adsorption and decomposition can be observed by visual check.

The material to be treated is only required to contain urethane and is not limited to particular materials. Examples of the material to be treated include the ground and waste (waste water) containing urethane, particularly, polyurethane.

The effect of decomposing the material to be treated is higher when the surface thereof is not subjected to coating, such as barrier-coating. However, even in the case of using the barrier-coated material to be treated, the decomposition can be sufficiently performed by the urethane decomposing method of the present invention.

Any unsaturated fatty acid can be used as the unsaturated fatty acid so long as it contains at least one double bond in the structure. The unsaturated fatty acid is preferably in a liquid form under the temperature conditions to be used of the room temperature because the material to be treated is treated easily. In this case, the room temperature is, for example, about 0° C. to about 35° C.

Examples of the unsaturated fatty acid include oleic acid, linoleic acid, palmitoleic acid, α-linolenic acid, γ-linolenic acid, arachidonic acid, docosahexaenoic acid (DHA), erucic acid, obtusilic acid, linderic acid, palmitoleic acid, and elaidic acid. These unsaturated fatty acids may be used alone or in a combination of two or more of them.

As the unsaturated fatty acid, an unsaturated fatty acid containing one double bond in the structure is more preferable than an unsaturated fatty acid containing two or more double bonds in the structure.

Among the unsaturated fatty acids, oleic acid, erucic acid, and linoleic acid can be particularly preferably used.

Examples of the method for treating the material to be treated using the unsaturated fatty acid include a method in which the material to be treated is immersed in the unsaturated fatty acid and a method in which the unsaturated fatty acid is applied to the material to be treated. Specifically, the method in which the material to be treated is immersed in the unsaturated fatty acid is preferable because the unsaturated fatty acid can be made to act on the entire material to be treated, and the method is simple.

The longer the time of treating the material to be treated using the unsaturated fatty acid, the better. However, the effect can be obtained even when the time is about several seconds. In order to obtain a higher effect, the material to be treated is preferably treated for 1 hour or more. Moreover, when the urethane decomposing method of the present invention is industrially used, the time is about 48 hours at longest because treating the material to be treated for a long period of time is disadvantageous. From these viewpoints, the time of treating the material to be treated using the unsaturated fatty acid is more preferably 8 hours or more to 24 hours or less.

The temperature at which the material to be treated is treated using the unsaturated fatty acid is not limited to particular temperatures and is preferably in a temperature range in which the unsaturated fatty acid is maintained to be in a liquid form. For example, in the case of using oleic acid or linoleic acid as the unsaturated fatty acid, the material to be treated may be treated at about 30° C.

When the material to be treated is treated using the unsaturated fatty acid, the unsaturated fatty acid is preferably used after mixing with alcohol. Generally, the viscosity of the unsaturated fatty acid is high, and the handling of the unsaturated fatty acid is difficult. However, when the unsaturated fatty acid is mixed with alcohol, the viscosity is reduced, and thus, the handleability is improved. When the viscosity of the treatment solution obtained by mixing the unsaturated fatty acid and alcohol is reduced, the phenomenon where the materials to be treated immersed in the treatment solution aggregate and fix one another can be suppressed. Accordingly, stable treating with little variations can be performed. Moreover, the treatment solution with a low viscosity quickly permeates into the material to be treated. Thus, not only the surface of the material to be treated, but also the entire material to be treated, can be treated.

By making the treatment solution obtained by mixing the unsaturated fatty acid and alcohol to act on the material to be treated as described above, physical properties such as breaking stress and stretch rate of the material to be treated can be significantly reduced. When the microorganism is made to act on the material to be treated, the material to be treated crushed into pieces as small as possible provides higher decomposition efficiency, compared with lumps of the material to be treated without being crushed. Thus, the material to be treated having reduced physical properties such as breaking stress and stretch rate is preferable because it can be crushed easily.

By making the microorganism to act on the material to be treated in which not only the surface but also the inside thereof have been sufficiently treated with the unsaturated fatty acid, the decomposition can progress uniformly to the inside of the material to be treated. When the decomposition sufficiently progresses to the inside of the material to be treated, the material to be treated after making the microorganism to act thereon can be easily crushed into powder.

By using the treatment solution obtained by mixing the unsaturated fatty acid and alcohol, an effect of washing the surface of the material to be treated can also be obtained. A silicone-based parting agent and an acrylurethane-based barrier coat are adhered to the surface of the urethane-containing material to be treated in some cases. These adherents reduce the efficiency of decomposing the material to be treated using the microorganism. By using the treatment solution obtained by mixing the unsaturated fatty acid and alcohol in the case of using such material to be treated, the silicon-based parting agent and the acrylurethane-based barrier coat adhered to the surface of the material to be treated can be removed, and the reduction in efficiency of decomposing the material to be treated using the microorganism can be suppressed.

The kind of the alcohol is not limited to particular kinds, but an alcohol having a lower viscosity than the unsaturated fatty acid and sufficient affinity for dissolving the unsaturated fatty acid is preferable. Moreover, an alcohol having a high effect of washing the silicon-based parting agent and the acrylurethane-based barrier coat is preferable. In view of easy availability and the like, a lower alcohol is preferable. Specifically, a mixture of one or more kinds selected from the group consisting of methanol, ethanol, 1-propanol, 2-propanol, 1-butanol, 2-butanol, 2-methyl-1-butanol, and 2-methyl-2-butanol can be preferably used.

The mixing ratio between the unsaturated fatty acid and the alcohol is preferably 1:9 to 7:3, more preferably 3:7 to 6:4, yet more preferably 5:5 as a volume ratio, in order to reduce the amount of adsorption of the unsaturated fatty acid as much as possible in the post step.

In the case of using the alcohol for the purpose of washing the surface of the material to be treated, the material to be treated may be washed using the alcohol before treating the material to be treated using the unsaturated fatty acid. In this case, the material to be treated is immersed into the alcohol and is then washed by, for example, shaking, and subsequently, the unsaturated fatty acid or a mixture of the unsaturated fatty acid and the alcohol may be made to act on the material to be treated.

Step of Making Microorganism to Act on Material to be Treated

The microorganism made to act on the material to be treated is only required to be a microorganism exhibiting urethane decomposing function and is not limited to particular microorganisms. However, a microorganism exhibiting sufficiently high urethane decomposing function is preferable. The inventors of the present invention found a microorganism belonging to a *Streptomyces* genus as such microorganism. In the present invention, this microorganism (see Japanese Patent Publication No. 2010-220610) can be preferably used.

A microorganism (*Streptomyces* C13a, *Streptomyces albogriseolus*) specified by Accession No. FERN BP-21770 can be given as an example of the microorganism that can be used in the present invention. The microorganism was deposited with the International Patent Organism Depositary, National Institute of Technology and Evaluation (#120, 2-5-8 Kazusakamatari, Kisarazu-shi, Chiba 292-0818, Japan) on Feb. 12, 2009 under the above-described Accession No. The genus of the deposited microorganism is *Streptomyces*, and the species is *S. albogriseolus*. The mutants of the microorganism also can be preferably used in the present invention as long as exhibiting the same urethane adsorbing capacity and urethane decomposing capacity. Specifically, for example, *S. albogriseolus* (NBRC12834), *S. thermoluteus* (NBRC14269), *S. viridodiastaticus* (NBRC13106), and the like can be preferably used.

The urethane decomposing method of the present invention in the case of using the microorganism specified by Accession No. FERM BP-21770 as an example is described below.

The method for making the microorganism to act on the material to be treated is only required to be a method in which the material to be treated and the microorganism are caused to be in contact with each other and is not limited to particular methods. For example, the method can be a method in which the material to be treated is added to a culture medium in which the microorganism is incubated, and the incubation is continued. The material to be treated may be added to a culture medium containing no microorganism, and the microorganism is then newly inoculated.

The microorganism belonging to a *Streptomyces* genus is a soil bacterium and thus has high growth ability in a simple medium containing carbon and an inorganic salt at a relatively low temperature and can be incubated by a simple method (general shaking culture). Moreover, the microorganism can survive in a hostile environment by forming a spore and generally generate an antibacterial compound. Thus, the microorganism has an advantage of having a high survival rate in a hetero microorganism environment. A medium and a method for incubating the microorganism can be those described in Japanese Patent Publication No. 2010-220610.

The longer the time of making the microorganism to act on the material to be treated, the better. This action may be performed so as to sufficiently decompose urethane by considering the content of urethane in the material to be treated and the amount of the microorganism to be made to act on the material to be treated.

The temperature at which the microorganism is made to act on the material to be treated is a temperature appropriate for growing the microorganism and decomposing urethane, for example, 26° C. to 45° C., preferably about 30° C. to about 45° C.

In the urethane decomposing method of the present invention, it is preferred that the microorganism is made to act on the material to be treated while treating the material to be treated using the unsaturated fatty acid, i.e., the microorganism is made to act on the material to be treated in the presence of the unsaturated fatty acid. For example, the unsaturated fatty acid and the material to be treated may be added to a culture medium of the microorganism, and the microorganism may be incubated. At that time, the concentration of the unsaturated fatty acid may be 0.1% (W/V) or less.

With this method, urethane contained in the material to be treated can be decomposed by a simpler method.

Urethane Decomposing Agent

The urethane decomposing agent of the present invention contains the microorganism and the unsaturated fatty acid.

The microorganism is inoculated to an appropriate medium (culture medium), and the unsaturated fatty acid is then added to the medium. This can be used as the urethane decomposing agent. The microorganism can be immobilized on a carrier according to a known method. In this case, the microorganism may be adsorbed on the surface of an appropriate porous carrier so as not to impair the action of the microorganism on urethane. The immobilized microorganism can be recovered and recycled after the use thereof. For example, a wettable powder obtained by adding a porous carrier such as clay to a culture medium containing the microorganism and the unsaturated fatty acid is prepared, and this wettable powder can be used as the urethane decomposing agent.

The urethane decomposing agent of the present invention may contain other components for assisting the growth of the microorganism and the decomposition and the adsorption of urethane in the range of not impairing the purpose of the present invention and can contain, for example, esterase.

The urethane decomposing agent of the present invention may contain the microorganism which is freeze-dried or immobilized and the unsaturated fatty acid.

The urethane decomposing agent of the present invention preferably further contains alcohol. Alcohol has bactericidal action on microorganisms, and thus, when the urethane decomposing agent contains alcohol, this alcohol is required not to be in contact with the microorganism.

When the alcohol and the unsaturated fatty acid are separately made to act on the material to be treated, the urethane decomposing agent may be a decomposing agent kit in which the alcohol and the unsaturated fatty acid are made to act on the material to be treated, and the microorganism is thereafter made to act on the material to be treated. In the case of the decomposing agent containing a treatment solution obtained by mixing the alcohol and the unsaturated fatty acid, the urethane decomposing agent may be a decomposing agent kit in which the treatment solution is made to act on the material to be treated, the material to be treated is then washed, and the microorganism is thereafter made to act on the material to be treated.

EXAMPLES

The present invention is described in more detail below with reference to the examples. The present invention, however, is not limited by these examples.

Example 1

(Material to be Treated)

A small piece was provided as a urethane-containing material to be treated. When a certain type of steering wheel made of polyurethane is subjected to RIM molding, as a protective film for protection by covering the surface of a rim part that performs a grip operation, a barrier coat is sprayed on a part (cavity) in which a molded product is formed. This small piece was cut out from a burr molded by integrating a barrier coat that adheres to an adjacent mating surface (parting surface) at the time of spraying the barrier coat and a urethane reaction solution thinly leaking and spreading on the parting surface. The small piece obtained by cutting a burr to have a size of about 40 mm×10 mm was used as the material to be treated. The thickness of the material to be treated was about 0.3 mm to about 0.5 mm. The barrier coat applied to the surface of the small piece was an acryl urethane-based coating material, and the coating with the barrier coat was performed so as to have a thickness of 10 to 20 μm.

(Unsaturated Fatty Acid)

Oleic acid (available from Wako Pure Chemical Industries, Ltd., Grade: Wako 1st Grade) was used as an unsaturated fatty acid.

(Microorganisms)

A microorganism (cell line: C13a) specified by Accession No. FERM BP-21770 was used as a microorganism exhibiting a urethane adsorbing capacity and a urethane decomposing capacity.

(Medium)

A YES-G medium prepared as described below was used as a medium for incubating the microorganism.

A $KH_2PO_4$ solution and a $Na_2HPO_4$ solution having the concentrations shown in Table 1 below were prepared, and 10 mL of the $KH_2PO_4$ solution and 40 mL of the $Na_2HPO_4$ solution were mixed, to prepare a Solution A. Other Solution B, Solution C, and Solution D were prepared so as to each have the composition shown in Table 1 below. The prepared Solutions A to D were subjected to a sterilization treatment under the conditions of 121° C. for 20 minutes.

20 mL of the Solution A, 4.0 g of gelatin, 970 mL of distilled water, and 0.5 g of $(NH_4)_2SO_4$ were introduced into a 3 L-capacity Erlenmeyer flask, then mixed, and subjected to a sterilization treatment under the conditions of 121° C. for 20 minutes. The resultant solution was cooled, and 10 mL of the Solution B, 0.1 mL of the Solution C (10 times concentration), and 2 mL of the Solution D were added to this 3 L-capacity Erlenmeyer flask. Thus, a YES-G medium was produced.

TABLE 1

| Solution name | Containing reagent | Content |
|---|---|---|
| Solution A | $KH_2PO_4$ | 0.182 g/20 mL (DW) |
|  | $Na_2HPO_4$ | 0.379 g/40 mL (DW) |
| Solution B | $MgSO_4 \cdot 7H_2O$ | 0.5 g/10 mL (DW) |
| Solution C | $MnCl_2 \cdot 4H_2O$ | 2.0 g |
| (10 times concentration) | $CuCl_2 \cdot 2H_2O$ | 0.028 g |
|  | $ZnCl_2$ | 0.022 g |
|  | $Na_2MoO_4 \cdot 2H_2O$ | 0.026 g |
|  | $FeCl_3 \cdot 6H_2O$ | 0.15 g |
|  | DW | 100 mL |
| Solution D | Yeast extract | 0.1 g/10 mL |

* In Table 1, "DW" indicates distilled water.

Step of Treating Material to be Treated Using Unsaturated Fatty Acid

About 60 mL of oleic acid was added to a 100 mL-capacity Erlenmeyer flask. 40 materials to be treated were provided and were introduced into the 100 mL-capacity Erlenmeyer flask, and the Erlenmeyer flask was covered using an aluminum foil and then left at normal temperature. A treatment using oleic acid was performed for 1 hour.

After the elapse of the treatment time, the inside of the Erlenmeyer flask was washed using tap water and distilled water, distilled water was thereafter further added to the Erlenmeyer flask, and the Erlenmeyer flask was washed with ultrasound. The materials to be treated were taken out from the Erlenmeyer flask and then further washed using distilled water. Then, the materials to be treated were sufficiently dried (overnight) at 40° C.

The weights of the materials to be treated were measured, and the 10 materials to be treated each were introduced into each of four 100 mL-capacity Erlenmeyer flasks and were then subjected to a sterilization treatment under the conditions of 121° C. for 20 minutes.

Materials treated for treatment times of 8 hours, 24 hours, and 48 hours using oleic acid were prepared by the same operation.

Step of Making Microorganism to Act on Material to be Treated

The microorganism (C13a) was inoculated in 100 mL of YES-G medium, and the medium was then subjected to shaking culture. Thus, preculture solution was obtained. The incubation conditions were at 40° C. and 140 rpm for 11 days.

10 mL of the preculture solution obtained as described above was added to 1 L of YES-G medium, and the medium was then subjected to shaking culture. Thus, main bacterial culture was obtained. The incubation conditions were at 40° C. and 140 rpm for 9 days.

50 mL of the main bacterial culture was dispensed into each of the above-provided 100 mL-capacity Erlenmeyer flask each containing the 10 materials to be treated, and the flasks were then subjected to shaking culture. The incubation conditions were at 40° C. and 80 rpm.

The incubation was performed so that the times of making the microorganism to act on the materials treated for the treatment times of 1 hour, 8 hours, 24 hours, and 48 hours using oleic acid, were 7 days, 14 days, 28 days, and 63 days.

Evaluation

After the elapse of the incubation periods, the bacterial cultures were discarded, and the materials to be treated were rinsed using distilled water and then washed with ultrasound. The materials to be treated were further washed using distilled water and sufficiently dried (overnight) at 40° C.

The weights of the materials to be treated were measured, and the weight loss rates (%) were calculated by comparing with the weights before making the microorganism to act on the materials to be treated.

The procedure was repeated a total of two times, and the results of the weight loss rates (%) are shown in Table 2 below.

TABLE 2

| Incubation period (day) | Count/Average | Oleic acid-treating time (hour) | | | |
|---|---|---|---|---|---|
| | | 1 | 8 | 24 | 48 |
| 7 | First time | 11.22 | 15.35 | 12.76 | 13.45 |
| | Second time | 12.14 | 10.21 | 16.73 | 14.51 |
| | Average | 11.68 | 12.78 | 14.75 | 13.98 |
| 14 | First time | 17.57 | 14.72 | 11.96 | 13.56 |
| | Second time | 16.57 | 19.13 | 16.83 | 15.86 |
| | Average | 17.07 | 16.93 | 14.40 | 14.71 |
| 28 | First time | 24.42 | 22.24 | 17.09 | 17.26 |
| | Second time | 23.51 | 29.20 | 27.70 | 17.49 |
| | Average | 23.97 | 25.72 | 22.40 | 17.38 |
| 63 | First time | 31.73 | 37.98 | 39.49 | 29.62 |
| | Second time | 24.45 | 37.19 | 37.18 | 42.41 |
| | Average | 28.09 | 37.59 | 38.34 | 36.02 |

Comparative Example 1

The materials to be treated were treated in the same manner as in Example 1 except that the microorganism (C13a) was made to act on the materials to be treated without pretreating them using oleic acid. The results of the weight loss rates (%) are shown in Table 3 below.

TABLE 3

| Count/Average | Incubation period (day) | | | |
|---|---|---|---|---|
| | 7 | 14 | 28 | 63 |
| First time | 0.76 | 1.01 | 1.23 | 1.63 |
| Second time | 3.49 | 4.69 | 4.74 | 5.54 |
| Average | 2.13 | 2.85 | 2.99 | 3.59 |

Comparative Example 2

The materials to be treated were treated in the same manner as in Example 1 except that the pretreatment using oleic acid was performed for 24 hours, and a YES-G medium to which the microorganism had not been added was made to act on the material to be treated. The results of the weight loss rates (%) are shown in Table 4 below.

TABLE 4

| Oleic acid-treating time (hour) | Treatment time (day) | | | |
|---|---|---|---|---|
| | 7 | 14 | 28 | 63 |
| 24 | 0.58 | 0.94 | 1.24 | 1.36 |

Example 2

The materials to be treated were treated in the same manner as in Example 1 except that linoleic acid (available from Wako Pure Chemical Industries, Ltd., Wako 1st grade) was used as a substitute for oleic acid, and a treatment using linoleic acid was performed for 24 hours while shaking. The results of the weight loss rates (%) are shown in Table 5 below.

TABLE 5

| Count/Average | Linoleic acid-treating time (hour) | Incubation period (day) | | |
|---|---|---|---|---|
| | | 7 | 28 | 69 |
| First time | 24 | 2.15 | 7.09 | 7.36 |
| Second time | | 1.85 | 5.89 | 9.33 |
| Average | | 2.05 | 6.50 | 8.35 |

Comparative Example 3

The microorganism was made to act on the materials to be treated in the same manner as in Example 1 except that a treatment using pretreatment agents shown in Table 6 below as a substitute for oleic acid was performed for 24 hours while shaking, or the treatment using the pretreatment agents was not performed. The results of the weight loss rates (%) are shown in Table 6 below.

TABLE 6

| Incubation period (day) | Count/Average | Agent (Treatment time: 24 hours) | | | | | | |
|---|---|---|---|---|---|---|---|---|
| | | Untreated | Acetic acid | Butanol | Calcium hydroxide | Glycerin | Hair lotion | Armor oil |
| 7 | First time | 1.16 | 0.42 | 0.15 | 0.77 | 1.06 | 1.22 | 1.40 |
| | Second time | 1.20 | 0.96 | 0.55 | 1.13 | 1.20 | 0.83 | 1.23 |
| | Average | 1.20 | 0.70 | 0.40 | 0.95 | 1.15 | 1.00 | 1.30 |
| 14 | First time | 1.44 | 0.65 | 0.42 | 1.12 | 1.43 | 1.51 | 1.45 |
| | Second time | 1.82 | 1.58 | 1.08 | 1.79 | 1.61 | 1.37 | 1.56 |
| | Average | 1.60 | 1.15 | 0.75 | 1.45 | 1.50 | 1.45 | 1.55 |
| 69 | First time | 2.04 | 1.24 | 0.90 | 1.99 | 2.45 | 2.22 | 2.48 |
| | Second time | 2.34 | 1.79 | 1.30 | 1.76 | 1.89 | 1.41 | 1.93 |
| | Average | 2.19 | 1.52 | 1.10 | 1.88 | 2.17 | 1.82 | 2.21 |

As acetic acid, 5% acetic acid obtained by mixing acetic acid (Special grade) and distilled water was used, and as calcium hydroxide, a saturated solution obtained by dissolving calcium hydroxide (Special grade) in distilled water was used. As a hair lotion, a hair lotion containing labeled ingredients of "ethanol, water, PPG-40 butyl, DPG" was used. As Armor oil, an Armor oil containing labeled ingredients of "silicone, an emulsifier, and a surfactant" and having a neutral pH was used.

Example 3

The materials to be treated were treated in the same manner as in Example 2 except that a molded burr obtained by the same manner as in Example 1 except that the barrier coat was not used as the urethane-containing materials to be treated, and oleic acid and linoleic acid were used as the unsaturated fatty acid, a treatment using the unsaturated fatty acid was performed for 24 hours. The results of the weight loss rates (%) are shown in Table 7 below.

TABLE 7

| Incubation | Count/ | Unsaturated fatty acid (treatment time: 24 hours) | |
|---|---|---|---|
| period (day) | Average | Oleic acid | Linoleic acid |
| 7 | First time | 21.05 | 4.35 |
|   | Second time | 26.74 | 14.10 |
|   | Average | 23.90 | 9.23 |
| 28 | First time | 40.31 | 12.13 |
|   | Second time | 23.56 | 18.95 |
|   | Average | 31.94 | 15.54 |
| 63 | First time | 58.85 | 6.24 |
|   | Second time | 48.66 | 20.39 |
|   | Average | 53.76 | 13.32 |

Comparative Example 4

The microorganism was made to act on the materials to be treated in the same manner as in Example 1 except that the materials to be treated described in Example 3 were used, a treatment was performed for 24 hours using the pretreatment agents described in Comparative Example 3 while shaking or the treatment using the pretreatment agent was not performed. The results of the weight loss rates (%) are shown in Table 8 below.

TABLE 8

| Incubation | Count/ | Agent (treatment time: 24 hours) | | | | |
|---|---|---|---|---|---|---|
| period (day) | Average | Untreated | Acetic acid | Butanol | Calcium hydroxide | Glycerin |
| 7 | First time | 0.81 | 0.86 | 0.06 | 0.31 | 0.75 |
|   | Second time | 0.86 | 0.15 | 0.44 | 0.93 | 0.64 |
|   | Average | 0.84 | 0.51 | 0.25 | 0.62 | 0.70 |
| 14 | First time | 1.55 | 1.63 | 0.91 | 0.94 | 1.56 |
|   | Second time | 1.12 | 0.67 | 0.71 | 0.95 | 0.79 |
|   | Average | 1.34 | 1.15 | 0.81 | 0.95 | 1.18 |
| 63 | First time | 1.44 | 1.56 | 1.04 | 1.58 | 1.56 |
|   | Second time | 1.23 | 0.74 | 0.82 | 1.16 | 0.96 |
|   | Average | 1.34 | 1.15 | 0.93 | 1.37 | 1.26 |

Example 4

As the materials to be treated, the materials A to be treated (including a barrier layer) described in Example 1 or the materials B to be treated (having no barrier layer) described in Example 3 were used. The microorganism was made to act on the materials to be treated in the same manner as in Example 1 except that the treatment times using oleic acid were several seconds, 15 minutes, and 30 minutes. The results of the weight loss rates (%) were shown in Table 9 below.

TABLE 9

| Incubation | Material A to be treated | | | Material B to be treated | | |
|---|---|---|---|---|---|---|
| period (day) | Several seconds | 15 mins | 30 mins | Several seconds | 15 mins | 30 mins |
| 7 | 13.65 | 11.75 | 11.43 | 16.90 | 20.85 | 21.17 |
| 14 | 20.56 | 17.89 | 21.59 | 20.60 | 25.31 | 25.28 |
| 28 | 16.92 | 24.24 | 23.01 | 20.65 | 35.67 | 36.72 |

As the conditions under which the materials to be treated were treated using oleic acid for several seconds, the materials to be treated were introduced into a beaker, oleic acid was then poured into the beaker to immerse the materials to be treated, the oleic acid was thereafter stirred about three times using tweezers, and the oleic acid was removed. The subsequent washing treatment was performed in the same manner as in Example 1.

Example 5

(Microorganism)

As microorganisms belonging to a *Streptomyces* genus, exhibiting urethane decomposing function, three kinds of microorganisms of *S. albogriseolus* (NBRC12834), *S. thermoluteus* (NBRC14269), and *S. viridodiastaticus* (NBRC13106) were used.

(Medium)

As media for incubating the microorganisms, a YES-Go medium having the composition shown in Table 10 below and a YM medium having the composition shown in Table 11 below were prepared. Each medium was subjected to a sterilization treatment under the conditions of 121° C. for 20 minutes, and the pH of the YM medium was adjusted to 7.3.

TABLE 10

| Component | Content |
| --- | --- |
| $(NH_4)_2SO_4$ | 0.5 g |
| Gelatin | 4.0 g |
| $K_2HPO_4$ | 1.0 g |
| $KH_2PO_4$ | 0.5 g |
| $MgSO_4 \cdot 7H_2O$ | 0.5 g |
| $MnCl_2 \cdot 4H_2O$ | 2.0 mg |
| $CuCl_2 \cdot 2H_2O$ | 0.028 mg |
| $ZnCl_2$ | 0.022 mg |
| $CaCl_2 \cdot 2H_2O$ | 0.027 mg |
| $Na_2MoO_4 \cdot 2H_2O$ | 0.026 mg |
| $FeCl_3 \cdot 6H_2O$ | 0.15 mg |
| yeast extract | 0.02 g |
| Distilled water | 1.0 L |

TABLE 11

| Component | Content |
| --- | --- |
| Yeast Extract | 4 g |
| Malt Extract | 10 g |
| Glucose | 4 g |
| Distilled water | 1.0 L |

Step of Treating Material to be Treated Using Unsaturated Fatty Acid

Materials treated using oleic acid for a treatment time of 24 hours were prepared in the same manner as in Example 1.

Step of Making Microorganism to Act on Material to be Treated

<Incubation in YES-Go Medium>

S. albogriseolus was inoculated to 100 mL of YES-Go medium and was then subjected to shaking culture. Thus, a preculture solution was obtained. The incubation conditions were at 30° C. and 140 rpm for 11 days.

10 mL of the resultant preculture solution was added to 1 L of YES-Go medium, and the resultant mixture was then subjected to shaking culture. Thus, a main bacterial culture was obtained. The incubation conditions were at 30° C. and 140 rpm for 9 days.

50 mL each of the main bacterial culture was dispensed into each 100 mL-capacity Erlenmeyer flask containing 10 materials to be treated, provided above, and was then subjected to shaking culture. The incubation conditions were at 30° C. and 80 rpm. The incubation was performed for the times of making S. albogriseolus to act on the materials to be treated of 7, 14, and 63 days.

The microorganisms were made to act on the materials to be treated in the same manner as described above except that S. albogriseolus, S. thermoluteus, and S. viridodiastaticus were used.

As to S. thermoluteus, the incubation temperature was 40° C.

<Incubation in YM Medium>

The microorganisms were made to act on the materials to be treated in the same manner as described above except that the YM medium was used as a substitute for the YES-Go medium.

Evaluation

In the same manner as in Example 1, the materials to be treated after the elapse of the incubation periods were washed and dried, and the weight loss rates (%) were calculated by comparing with the weights before making the microorganism to act on the materials to be treated. The results are shown in Table 12.

TABLE 12

| | | Incubation period (day) | | |
| --- | --- | --- | --- | --- |
| | | 7 | 28 | 63 |
| S. albogriseolus | YES-Go | 16.3 | 32.4 | 34.8 |
| | YM | 5.1 | 21.0 | 44.4 |
| S. thermoluteus | YES-Go | 19.3 | 19.8 | 34.2 |
| | YM | 3.5 | 5.4 | 29.9 |
| S. viridodiastaticus | YES-Go | 14.4 | 21.1 | 30.3 |
| | YM | 8.0 | 25.0 | 46.5 |

Comparative Example 5

Each microorganism was made to act on the materials to be treated in the same manner as in Example 5 except that the materials to be treated were not treated using oleic acid in Example 5. The weight change rates (%) were calculated from the change between the weights of the materials to be treated before and after making each microorganism to act on the materials to be treated. The results are shown in Table 13.

TABLE 13

| | | Incubation period (day) | | |
| --- | --- | --- | --- | --- |
| | | 7 | 28 | 63 |
| S. albogriseolus | YES-Go | 0.8 | 0.8 | 1.5 |
| | YM | 1.4 | 0.6 | 0.1 |
| S. thermoluteus | YES-Go | 1.4 | 1.4 | 2.2 |
| | YM | 0.9 | 0.7 | 0.2 |
| S. viridodiastaticus | YES-Go | 1.0 | 1.2 | 2.3 |
| | YM | 1.1 | 1.4 | 3.6 |

Example 6

Oleic acid and ethanol were mixed at the mixing ratios shown in Table 14 below to produce treatment solutions, and the viscosities of the treatment solutions were then measured. The results demonstrated that the viscosities of the treatment solutions containing 50 volume % or more ethanol were sufficiently reduced. The results are shown in Table 14.

TABLE 14

| Ratio (Volume ratio) Oleic acid:Ethanol | Viscosity (20° C.) MPa · s |
| --- | --- |
| 100:0 | 31 |
| 50:50 | 15 |
| 25:75 | 8 |
| 10:90 | 4 |
| 0:100 | 1.2 |

The same materials to be treated as used in Example 1 were immersed in the treatment solution having the mixing ratio between oleic acid and ethanol of 50:50, produced above, and the treatment solution was made to act on the materials to be treated for 24 hours. The surfaces of the materials to be treated were subjected to acrylurethane-based barrier coating. A silicone-based parting agent was further adhered thereto. A skin layer having a low molecular weight was formed on each of the topmost surfaces of the materials to be treated.

These materials to be treated were subjected to measurement by infrared spectroscopy before and after making the treatment solution to act thereon. The results showed that a peak showing a structure of Si—O—Si at the neighborhood of 1020 cm$^{-1}$ and a peak showing the structure of Si—CH$_3$ at 780 cm$^{-1}$ were detected in the materials to be treated before making the treatment solution to act thereon, and the results demonstrated that the components of the parting agent were adhered. On the other hand, the peaks at the neighborhood of 1020 cm$^{-1}$ and 780 cm$^{-1}$ were not detected in the materials to be treated after making the treatment solution to act thereon, and the results demonstrated that the components of the parting agent were released.

Furthermore, how to change the surfaces of the materials to be treated in the course of making the treatment solution to act thereon was checked using a microscope. The results showed that the surfaces of the materials to be treated were smooth before making the treatment solution to act thereon, the topmost surfaces were a little rough after making the treatment solution to act thereon for 1 hour, and the topmost surfaces were again smooth after making the treatment solution to act thereon for 24 hours. This demonstrated that the barrier-coated skin layer formed on the topmost surface could be removed by making the treatment solution of oleic acid containing 50 volume % ethanol to act on the material to be treated. The skin layer serves as reducing environmental burdens from the outside and protecting physical properties of the material. Thus, by removing this skin layer, the decomposition of the material to be treated can be accelerated. It is considered that the material having a low molecular weight is easily dissolved in a solvent such as alcohol, and thus, the skin layer could be removed by the pretreatment.

As physical properties of the material to be treated which is pretreated as described above, the braking stress and the stretch rate were measured. The results showed that the stretch rate after two weeks was 112%, the stretch rate after four weeks was 83%, the breaking stress after two weeks was 0.99 N/mm$^2$, and the breaking stress after four weeks was 0.75 N/mm$^2$.

In the case of treating the materials to be treated using only oleic acid, the stretch rate after two weeks was 106%, the stretch rate after four weeks was 118%, and the breaking stress after two weeks was 0.89 N/mm$^2$, and the breaking stress after four weeks was 0.96 N/mm$_2$.

Accordingly, it was demonstrated that in the case of using oleic acid after adding ethanol, after two weeks, the physical properties of the materials to be treated were reduced as in the case of treating the materials using only oleic acid, and after four weeks, the physical properties of the materials to be treated were largely reduced, compared with the case of treating the materials using only oleic acid. This is because, by using a treatment solution obtained by adding alcohol to unsaturated fatty acid, the oleic acid quickly permeates into and is made to act on the inside of the materials to be treated.

The microorganism (C13a) was made to act on the material to be treated which is pretreated as described above in the same manner as in Example 1. The weight loss rate after one week was 14.0%, the weight loss rate after two weeks was 18.2%, and the weight loss rate after four weeks was 20.4%.

Example 7

Oleic acid, erucic acid, linoleic acid, and linolenic acid were mixed with ethanol respectively to produce treatment solutions. The mixing was performed so as to have a mixing ratio between each unsaturated fatty acid and ethanol of 50:50 as a volume ratio.

The materials to be treated used in Example 1 were immersed in the treatment solutions in the same manner as in Example 6, and the treatment solutions were made to act on the materials to be treated for 24 hours.

The materials to be treated were then washed and dried, and the microorganism (C13a) was thereafter made to act on the materials to be treated in the same manner as in Example 1. The results demonstrated that the decomposition efficiencies by the microorganism were higher in the case of using oleic acid and erucic acid each having one double bond in the structure, compared with the case of using fatty acid having two or more double bonds. The results are shown in Table 15.

TABLE 15

| Treatment solution | Carbon | The number | Melting | Weight loss rate (%) | | |
|---|---|---|---|---|---|---|
| Mixing ratio (50 volume %) | number | of double bonds | point (° C.) | After one week | After two weeks | After four weeks |
| Oleic acid/Ethanol | 18 | 1 | 15 | 14.0 | 18.9 | 20.7 |
| Erucic acid/Ethanol | 22 | 1 | 28~32 | 16.3 | 23.2 | 27.9 |
| Linoleic acid/Ethanol | 18 | 2 | −5 | 2.1 | 3.5 | 6.5 |
| Linolenic acid/Ethanol | 18 | 3 | −11 | 4.5 | 3.3 | 4.1 |

Example 8

The same materials to be treated as used in Example 1 were prepared, washed three times using distilled water, and subsequently subjected to ultrasound washing using distilled water for 15 minutes. The materials were wrapped in paper towel and were dried at 40° C. for 24 hours.

The weights of the materials to be treated were measured and subsequently subjected to autoclave sterilization treatment under the conditions of 121° C. for 20 minutes.

Media obtained by adding oleic acid to the YES-Go medium so as to have 0.01 (w/v) %, 0.10 (w/v) %, and 1.0 (w/v) % were prepared. C13a was inoculated into media, and the materials to be treated after sterilization treatment were added thereto, and the resultant mixtures were then incubated. The incubation conditions were at 40° C. and 80 rpm.

The materials to be treated were recovered three times after one week, two weeks, and four weeks after the incubation, were then washed three times using distilled water, and were subsequently subjected to ultrasound washing for 15 minutes using distilled water. The materials were wrapped in paper towel and were dried at 40° C. for 24 hours. The weights of the materials to be treated after the drying were measured, and the weight change rates were calculated based on the weights before being added to the medium. The results are shown in Table 16.

TABLE 16

| The proportion of oleic acid to be added (w/v) | | Before treatment | After one week | After two weeks | After four weeks |
|---|---|---|---|---|---|
| 0.01% | C13a | 0 | 1.2 | 1.2 | 0.3 |
| | Only medium | 0 | −0.5 | −0.5 | 0.1 |
| 0.10% | C13a | 0 | 1.6 | 0.2 | 0.1 |
| | Only medium | 0 | 6.8 | 7.5 | 5.1 |
| 1.00% | C13a | 0 | 45.8 | 28.8 | 2.8 |
| | Only medium | 0 | 73.4 | 72 | 71.1 |

As shown in Table 16, the weights of the materials to be treated added to the media having large amounts of oleic acid to be added were largely increased, and this demonstrated that oleic acid was adsorbed to the materials to be treated. On the other hand, even when the amount of oleic acid to be added was the same, in the case of containing C13a, the decomposition of the materials to be treated progressed. Thus, the weight increase rates were reduced as the elapse of the incubation period to two weeks, four weeks.

As described above, it was demonstrated that, even in the case of not treating the materials to be treated using an unsaturated fatty acid in advance, by making the unsaturated fatty acid to act on the materials to be treated at the time of making the microorganism to act thereon, the decomposition of urethane can be accelerated.

What is claimed is:

1. A urethane decomposing method comprising the steps of: treating a urethane-containing material by immersing the urethane-containing material in a treatment liquid containing an unsaturated fatty acid; and allowing a microorganism, belonging to a *Streptomyces* genus and exhibiting a urethane decomposing function, to act on the urethane-containing material treated with the unsaturated fatty acid.

2. The urethane decomposing method according to claim 1, wherein during the step of treating the urethane-containing material, the unsaturated fatty acid and an alcohol are mixed together.

3. The urethane decomposing method according to claim 2, wherein the alcohol is a mixture of one or more kinds selected from the group consisting of methanol, ethanol, 1-propanol, 2-propanol, 1-butanol, 2-butanol, 2-methyl-1-butanol, and 2-methyl-2-butanol.

4. The urethane decomposing method according to claim 1, including a step of treating the urethane-containing material with an alcohol before the step of treating the urethane-containing material with the unsaturated fatty acid.

5. The urethane decomposing method according to claim 1, wherein the microorganism belonging to the *Streptomyces* genus is a microorganism specified by Accession No. FERM BP-21770.

6. The urethane decomposing method according to claim 1, wherein the unsaturated fatty acid is a mixture of one or more kinds selected from the group consisting of oleic acid, linoleic acid, and erucic acid.

7. The urethane decomposing method according to claim 1, wherein the step of allowing the microorganism to act on the urethane-containing material is carried out during the step of treating the urethane-containing material with the unsaturated fatty acid.

8. The urethane decomposing method according to claim 1, wherein the step of allowing the microorganism to act on the urethane-containing material includes adding the unsaturated fatty acid and the urethane-containing material to a culture medium of the microorganism.

9. The urethane decomposing method according to claim 1, wherein the step of allowing the microorganism to act on the urethane-containing material includes placing the microorganism in contact with the urethane-containing material treated with the unsaturated fatty acid.

10. The urethane decomposing method according to claim 1, consisting essentially of the steps of: treating the urethane-containing material by immersion in the treatment liquid and allowing the microorganism to act on the urethane-containing material.

11. A urethane decomposing method comprising the steps of immersing a urethane-containing material in a treatment liquid containing a liquid unsaturated fatty acid and allowing a microorganism belonging to a *Streptomyces* genus and exhibiting a urethane decomposing function to act on the treated urethane-containing material.

12. The urethane decomposing method according to claim 11, wherein the liquid unsaturated fatty acid has one double bond.

13. The urethane decomposing method according to claim 12, wherein the liquid unsaturated fatty acid is erucic acid.

14. The urethane decomposing method according to claim 11, wherein the liquid unsaturated fatty acid is at least one member selected from the group consisting of oleic acid, linoleic acid and erucic acid.

15. The urethane decomposing method according to claim 11, wherein the microorganism is at least one member selected from the group consisting of *Streptomyces albogriseolus*, *Streptomyces thermoluteus* and *Streptomyces viridodiastaticus*.

16. The urethane decomposing method according to claim 11, wherein the microorganism is *Streptomyces* C13a.

17. The urethane decomposing method according to claim 11, wherein the liquid unsaturated fatty acid is erucic acid and the microorganism is *Streptomyces* C13a.

18. The urethane decomposing method according to claim 11, consisting essentially of the steps of immersing the urethane-containing material in the treatment liquid and allowing the microorganism to act on the urethane-containing material.

19. A urethane decomposing agent containing the microorganism and the unsaturated fatty acid, according to claim 1.

20. The urethane decomposing agent according to claim 19, further containing an alcohol.

* * * * *